US009220640B2

(12) United States Patent
Ales et al.

(10) Patent No.: US 9,220,640 B2
(45) Date of Patent: Dec. 29, 2015

(54) ABSORBENT ARTICLE INCLUDING TWO DIMENSIONAL CODE MADE FROM AN ACTIVE GRAPHIC

(75) Inventors: Thomas Michael Ales, Neenah, WI (US); Andrew Mark Long, Appleton, WI (US); Matt Fitton, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 544 days.

(21) Appl. No.: 12/982,319

(22) Filed: Dec. 30, 2010

(65) Prior Publication Data
US 2012/0172825 A1 Jul. 5, 2012

(51) Int. Cl.
*A61F 13/42* (2006.01)
*A61F 13/84* (2006.01)
*G06Q 30/02* (2012.01)

(52) U.S. Cl.
CPC .............. *A61F 13/42* (2013.01); *A61F 13/84* (2013.01); *G06Q 30/0239* (2013.01); *A61F 2013/8497* (2013.01)

(58) Field of Classification Search
CPC . A61F 13/42; A61F 13/84; A61F 2013/8497; G06Q 30/0239
USPC .................. 604/318, 361; 40/625; 235/462.08
See application file for complete search history.

(56) References Cited

U.S. PATENT DOCUMENTS

| | | |
|---|---|---|
| 3,675,654 A | 7/1972 | Baker et al. |
| 3,731,685 A | 5/1973 | Eidus |
| 4,022,211 A | 5/1977 | Timmons et al. |
| 4,100,324 A | 7/1978 | Anderson et al. |
| 4,192,311 A | 3/1980 | Felfoldi |
| 4,292,916 A | 10/1981 | Bradley et al. |
| 4,327,731 A | 5/1982 | Powell |
| 4,366,241 A | 12/1982 | Tom et al. |
| 4,734,238 A | 3/1988 | Sugimori et al. |
| 4,812,053 A | 3/1989 | Bhattacharjee |
| 4,903,254 A | 2/1990 | Haas |
| 4,931,051 A | 6/1990 | Castello |
| 4,940,464 A | 7/1990 | Van Gompel et al. |
| 4,987,849 A | 1/1991 | Sherman |

(Continued)

FOREIGN PATENT DOCUMENTS

DE 10 2007 006 230 A1 8/2008
EP 2175398 4/2010

(Continued)

OTHER PUBLICATIONS

International Search Report for PCT IB2011 055137, Jul. 2012.

(Continued)

*Primary Examiner* — Lynne Anderson
*Assistant Examiner* — Peter S Vasat
(74) *Attorney, Agent, or Firm* — Dority & Manning, P.A.

(57) ABSTRACT

Absorbent articles are disclosed that convey information to a user. In particular, the absorbent articles include an active graphic that comprises a machine readable code. The active graphic, for instance, may comprise a disappearing graphic, an appearing graphic, and/or a color-change graphic. The change in appearance of the graphic may occur once contacted with a suitable activation agent, such as urine. The machine readable code contained in the active graphic, once scanned by a suitable reader device, may convey information to a user related to the absorbent article.

24 Claims, 4 Drawing Sheets

(56) References Cited

U.S. PATENT DOCUMENTS

| | | | |
|---|---|---|---|
| 5,006,711 A | 4/1991 | Hamashima et al. | |
| 5,045,283 A | 9/1991 | Patel | |
| 5,053,339 A | 10/1991 | Patel | |
| 5,058,088 A | 10/1991 | Haas et al. | |
| 5,089,548 A | 2/1992 | Zimmel et al. | |
| 5,284,703 A | 2/1994 | Everhart et al. | |
| 5,350,625 A | 9/1994 | Peterson et al. | |
| 5,352,582 A | 10/1994 | Lichtenwalter et al. | |
| 5,359,525 A | 10/1994 | Weyenberg | |
| 5,389,093 A | 2/1995 | Howell | |
| 5,486,166 A | 1/1996 | Bishop et al. | |
| 5,490,846 A | 2/1996 | Ellis et al. | |
| 5,645,542 A | 7/1997 | Anjur et al. | |
| 5,726,435 A | 3/1998 | Hara et al. | |
| 5,766,389 A | 6/1998 | Brandon et al. | |
| 5,820,973 A | 10/1998 | Dodge, II et al. | |
| 5,854,148 A | 12/1998 | Asada et al. | |
| 5,989,923 A | 11/1999 | Lowe et al. | |
| 6,200,765 B1 | 3/2001 | Murphy et al. | |
| 6,294,392 B1 | 9/2001 | Kuhr et al. | |
| 6,297,424 B1* | 10/2001 | Olson et al. | 604/361 |
| 6,307,119 B1 | 10/2001 | Cammarota et al. | |
| 6,362,389 B1 | 3/2002 | McDowall et al. | |
| 6,436,651 B1 | 8/2002 | Everhart et al. | |
| 6,508,797 B1 | 1/2003 | Pozniak et al. | |
| 6,610,386 B2 | 8/2003 | Williams et al. | |
| 6,645,190 B1 | 11/2003 | Olson et al. | |
| 6,706,342 B2 | 3/2004 | Kong et al. | |
| 6,710,221 B1 | 3/2004 | Pierce et al. | |
| 6,713,660 B1 | 3/2004 | Roe et al. | |
| 6,758,391 B1* | 7/2004 | Pickens, III | 235/375 |
| 6,772,708 B2 | 8/2004 | Klofta et al. | |
| 6,786,412 B2 | 9/2004 | Shimizu | |
| 6,904,865 B2 | 6/2005 | Klofta et al. | |
| 6,997,384 B2 | 2/2006 | Hara | |
| 7,181,066 B1* | 2/2007 | Wagman et al. | 382/183 |
| 7,195,165 B2 | 3/2007 | Kesler et al. | |
| 7,306,764 B2 | 12/2007 | Mody | |
| 7,321,315 B2 | 1/2008 | Brumm | |
| 7,332,642 B2 | 2/2008 | Liu | |
| 7,674,747 B1 | 3/2010 | Long | |
| 2001/0031954 A1 | 10/2001 | Jordan et al. | |
| 2002/0007162 A1 | 1/2002 | Cammarota et al. | |
| 2002/0062117 A1 | 5/2002 | Raufman et al. | |
| 2002/0114936 A1 | 8/2002 | Kong et al. | |
| 2002/0145525 A1 | 10/2002 | Friedman et al. | |
| 2004/0064113 A1* | 4/2004 | Erdman | 604/361 |
| 2004/0143234 A1 | 7/2004 | Nakahata et al. | |
| 2004/0246529 A1* | 12/2004 | Pruden et al. | 358/3.28 |
| 2005/0065489 A1 | 3/2005 | Driskell et al. | |
| 2005/0101841 A9 | 5/2005 | Kaylor et al. | |
| 2005/0112085 A1 | 5/2005 | MacDonald et al. | |
| 2005/0137542 A1 | 6/2005 | Underhill et al. | |
| 2005/0148961 A1 | 7/2005 | Sosalla et al. | |
| 2005/0148978 A1 | 7/2005 | Brumm et al. | |
| 2005/0217791 A1 | 10/2005 | Costello et al. | |
| 2005/0252967 A1 | 11/2005 | Kesler et al. | |
| 2006/0004333 A1* | 1/2006 | Olson | 604/361 |
| 2006/0020249 A1 | 1/2006 | Allen | |
| 2006/0149197 A1 | 7/2006 | Niemeyer | |
| 2006/0229577 A1 | 10/2006 | Roe et al. | |
| 2006/0293634 A1 | 12/2006 | Thomas et al. | |
| 2007/0071320 A1 | 3/2007 | Yada | |
| 2007/0079748 A1 | 4/2007 | Ahmed et al. | |
| 2007/0138286 A1 | 6/2007 | Kamijoh et al. | |
| 2007/0142795 A1 | 6/2007 | Cohen et al. | |
| 2007/0199994 A1 | 8/2007 | Cattrone et al. | |
| 2007/0259997 A1 | 11/2007 | Bakker et al. | |
| 2007/0270773 A1* | 11/2007 | Mackey | 604/361 |
| 2007/0278316 A1* | 12/2007 | Hovis | 235/494 |
| 2007/0282286 A1 | 12/2007 | Collins et al. | |
| 2008/0110984 A1 | 5/2008 | Uchitani | |
| 2008/0145945 A1* | 6/2008 | Song | 436/97 |
| 2008/0147031 A1 | 6/2008 | Long et al. | |
| 2009/0050700 A1 | 2/2009 | Kamijoh et al. | |
| 2009/0062757 A1 | 3/2009 | Long et al. | |
| 2009/0155753 A1 | 6/2009 | Ales et al. | |
| 2009/0247979 A1 | 10/2009 | Sosalla et al. | |
| 2009/0326491 A1 | 12/2009 | Long et al. | |
| 2010/0072271 A1 | 3/2010 | Thorstensson | |
| 2010/0164733 A1 | 7/2010 | Ales et al. | |
| 2010/0168694 A1 | 7/2010 | Gakhar et al. | |
| 2011/0015063 A1 | 1/2011 | Gil et al. | |
| 2011/0015597 A1 | 1/2011 | Gil et al. | |
| 2011/0183712 A1 | 7/2011 | Eckstein et al. | |

FOREIGN PATENT DOCUMENTS

| | | |
|---|---|---|
| JP | 4143876 A | 5/1992 |
| JP | 2003 058759 A | 2/2003 |
| JP | 2006 249638 A | 9/2006 |
| JP | 2008-264232 | 11/2008 |
| JP | 2009 280946 A | 12/2009 |
| WO | WO 96/08788 A1 | 3/1996 |
| WO | WO 00/37009 A2 | 6/2000 |
| WO | WO 00/65348 A2 | 11/2000 |
| WO | WO 2004/084765 A2 | 10/2004 |
| WO | WO 2008/072116 A1 | 6/2008 |
| WO | WO 2010/015881 A1 | 2/2010 |

OTHER PUBLICATIONS

IPRP for PCT IB2011 055137, Jul. 2012.
International Search Report for PCT IB2011 055165, Jul. 2012.
IPRP for PCT IB2011 055165, Jul. 2012.
Search Report for EP 11853168, mailed Nov. 5, 2014.
Search Report for EP 1852424, maiied Jan. 1, 2015.

* cited by examiner

ABSORBENT ARTICLE INCLUDING TWO DIMENSIONAL CODE MADE FROM AN ACTIVE GRAPHIC

BACKGROUND

Absorbent articles such as diapers, training pants, incontinence products, feminine hygiene products, and the like conventionally include a liquid permeable bodyside liner, a liquid impermeable outer cover, and an absorbent core. The absorbent core is typically located inbetween the outer cover and the liner for taking in and retaining body fluids exuded by the wearer, such as urine.

The absorbent core can be made of, for instance, superabsorbent particles. Many absorbent articles, especially those sold under the trade name HUGGIES™ by the Kimberly-Clark Corporation, are incredibly efficient at absorbing liquids and other body fluids. Absorbent articles today are also easier to don, are very comfortable to wear, prevent against leakage, and also provide or possess various other features and advantages not available previously.

Recently, those skilled in the art have suggested making absorbent articles interactive with the user and the caregiver. In particular, those skilled in the art have proposed incorporating features into the absorbent articles that convey information to the wearer and/or the caregiver. For instance, various different types of wetness sensing devices have been proposed for incorporation into absorbent articles. Wetness indicators may include alarm devices that are designed to assist parents or attendants identify a wet condition early on. The devices are designed to produce either a visible or an audible signal.

In U.S. Patent Application Publication No. 2009/0155753, which is incorporated by reference, a system for tracking behavior is described that can be used in conjunction with an absorbent article. In particular, one or more sensors may be incorporated into an absorbent article that provide information or data into a computing device for tracking the behavior of children or those wearing the absorbent article.

In U.S. Patent Application Publication No. 2009/0326491, which is also incorporated herein by reference, a method is disclosed for providing feedback to a caregiver regarding the progress that is being made in toilet training a child. The method, for instance, may be used to determine when to select a next generation product for facilitating toilet training.

The above products and methods have provided great advances in the art. Through the above products and methods, absorbent articles are not only capturing body fluids but are also becoming interactive by providing useful information to the wearer and/or caregiver during use of the product. A need still exists, however, for further advances in the evolution of absorbent articles and for using the absorbent article as a source of information. More particularly, a need exists for a new method of enabling access to or otherwise making available information to a user through the use of an absorbent article.

SUMMARY

In general, the present disclosure is directed to absorbent articles that include an information conveying device that can be easily applied to the article and that can provide the user with easy access to information that is related to the product. In one embodiment, for instance, the present disclosure is directed to applying a graphic to an absorbent article that comprises a machine readable code that, when read by a suitable reader device, provides information about the product. The information conveyed by the graphic, for instance, can be related to the health or another characteristic of the wearer, can provide information about proper use of the product, or can include promotional information for purchasing further units of the product or related products. In one embodiment, the graphic may comprise an active graphic that switches between a visible state and a state where the graphic is not readily noticeable until contacted with an activation agent.

The use of a graphic to provide access to information about the product offers various advantages and benefits. For instance, the graphic can be incorporated into the absorbent article without adding substantial cost to the article. As will be described in greater detail below, the graphic can also be incorporated into the article without substantially adversely impacting the overall aesthetic look of the product.

Prior to describing the embodiments of the present disclosure in detail, the following are definitions of various terms.

The term "active graphic" as used herein refers to an appearing graphic, a disappearing graphic, a color changing graphic or a combination thereof. The term "appearing graphic" is used herein to refer to a graphic that becomes visible (appears) or becomes significantly more visible when exposed to a body exudate. Conversely, the term "disappearing graphic" is used herein to refer to a graphic that becomes invisible (disappears) or significantly less visible when exposed to an activation agent, which, in one embodiment, may be a body exudate, such as urine, fecal matter, a vaginal secretion or a nasal discharge. In yet another embodiment, the active graphic may be a color changing graphic, or the active graphic changes color when exposed to an activation agent. In one embodiment, the active graphic may comprise a color changing graphic that is also an appearing graphic. For instance, the active graphic may initially match a background color and then, when activated, changes color to become visible. In yet another embodiment, the active graphic may comprise a color changing graphic that is also a disappearing graphic. In this embodiment, the active graphic may change color when contacted with an activation agent in order to match the background, leaving a negative of the image. In still another embodiment, the active graphic may be a combination of a disappearing graphic and an appearing graphic. For instance, a graphic may appear on the absorbent article and be covered by a disappearing graphic. When the disappearing graphic contacts an activation agent and disappears, the appearing graphic below becomes visible.

In particular embodiments, the active graphic can comprise a disappearing graphic which is formed from an ink that is soluble in aqueous solutions such as a body exudate. The ink is positioned in the absorbent article so that it becomes wet and dissolves when the product is insulted with a liquid. Once dissolved, the ink washes away from the outer cover and is obscured by the outer cover. As a result, the active graphic seems to disappear from view.

Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid.

A particular aqueous soluble ink composition is disclosed in U.S. Pat. No. 6,307,119, which is incorporated herein by reference. Active graphics may also be employed that appear over time due to exposure to time intervals, temperature levels, oxygen levels, etc., such as described in U.S. Pat. No. 5,058,088, U.S. Pat. No. 5,053,339, U.S. Pat. No. 5,045,283, U.S. Pat. No. 4,987,849, U.S. Pat. No. 4,903,254, U.S. Pat. No. 4,812,053, and U.S. Pat. No. 4,292,916, which are all incorporated herein by reference.

The active graphic can also comprise a color changing graphic which is formed from a composition such as an ink or adhesive that changes color when exposed to an aqueous solution such as urine. A color change composition can be adapted to blend in with a background or surrounding color, either before or after exposure to the aqueous solution or to undergo a more noticeable color change. Color changing graphics, for instance, may go from a first color to a second color, from a first color to clear, from clear to a color, or from a first shade to a second shade of a color. Suitable compositions of this color-change type are available from a variety of commercial vendors, such as a pH-change/color-change hot melt adhesive available from Findley Adhesives, Inc. of Wauwatosa, Wis., USA. Alternatively, the active graphic can comprise pH sensitive inks, fugitive inks, colored absorbent particles, hydratable salts, moisture sensitive films, enzymes, heat sensitive inks and dyes, or the like.

In one embodiment, a color changing active graphic composition may comprise a matrix-forming component, a colorant, a surfactant and a pH adjuster. The matrix-forming component may be a water-insoluble, film-forming polymer or an ink base, such as a flexographic varnish having an organic solvent base. The colorant can be a pH indicator, such as a charged pH indicator, capable of changing color in response to the presence of a fluid. The surfactant may include a charged surfactant that attracts the colorant or a combination of charged surfactants that attract the colorant and a neutral surfactant. The pH adjuster may include a low molecular weight organic acid and a high molecular weight organic acid.

The matrix-forming component may comprise, for instance, an acrylate/acrylamide copolymer, a polyurethane adhesive, methylcellulose, and/or copolymers of vinylpyrrolidone and dimethylaminopropyl methacrylamide. Such color changing compositions are disclosed, for instance, in U.S. patent application Ser. Nos. 12/503,364 or 12/503,380, which are incorporated herein by reference.

In another embodiment, a color-changing composition is used that is water-resistant and water-insoluble. The color-changing composition can form thin films of various patterns and shapes on a substrate upon drying and the films can generate color upon contact with an aqueous medium. In one embodiment, the composition includes various components dissolved in a volatile organic solvent medium. The components can comprise a leuco dye or a combination of leuco dyes, an electron-withdrawing color developer or a combination of color developers that can form color complexes when associated with the leuco dye under the proper conditions, and a separator or combination of separators, which when dissolved in the system in an adequate quantity, can prevent the formation of the color complexes. In one embodiment, the components can be contained within a polymeric encapsulation matrix. The encapsulating matrix can contain at least one kind of polymeric resin that can form a thin film on substrate surfaces with good adhesion. In addition to the above, the solution may also contain various other additives to adjust physical properties.

Leuco dyes are generally referred to as colorless or pale-colored basic dyes, because the dye molecules can acquire two forms, one of which is colorless. Although not intended to be bound by theory, it is believed that the color-developer agent functions as a Lewis acid, which withdraws electrons from the leuco dye molecule to generate a conjugated system. Hence, the leuco dye appears to manifest color from an originally colorless state.

For example, the Spiro form of an oxazine is a colorless leuco dye; the conjugated system of the oxazine and another aromatic part of the molecule is separated by an $sp^3$-hybridized "spiro" carbon. After protonating a part of the molecule, irradiation with UV-light or introducing other kind of such change, the bond between the Spiro carbon and the oxazine interrupts, the ring opens, the spiro carbon achieves $sp^2$ hybridization and becomes planar, the aromatic group rotates, aligns its π-orbitals with the rest of the molecule, and a conjugated system forms, with ability to absorb photons of visible light, and therefore appear colorful.

The leuco dyes that may be employed can be selected from a variety of dyes including, for example, phthalide leuco dyes, triarylmethane leuco dyes, and fluoran leuco dyes. Examples may include (1) Triarylmethane-based dyes, e.g. 3,3-bis(p-dimethylaminophenyl)-6-dimethylaminophthalide, 3,3-bis (p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide, etc. (2) Diphenylmethane-based dyes, e.g., 4,4'-bisdimethylaminobenzhydryl benzyl ether, N-halophenylleucoauramine, N-2,4,5-trichlorophenyl-leucoauramine, etc. (3) Lactam-based dyes, e.g., rhodamine-B-anilinolactam, rhodamine-(p-nitroanilino)lactam, rhodamine-(o-chloroanilino)lactam, etc. (4) Fluoran-based dyes, e.g., 3-dimethylamino-7-methoxyfluoran, 3-diethylamino-6-methoxyfluoran, 3-di-ethylamino-7-methoxyfluoran, 3-diethylamino-7-chlorofluoran, 3-diethylamino-6-methyl-7-chlorofluoran, 3-di-ethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino)fluoran, 3-diethylamino-6-methyl-7-phenylaminofluoran, 3-dibutylamino-6-methyl-7-phenylaminofluoran, 3-diethylamino-7-(2-carbomethoxyphenylamino) fluoran, 3-(N-cyclohexyl-N-methylamino)-6-methyl-7-phenylaminofluoran, 3-pyrrolidine-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino)fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-β-ethylhexylamino)-6-methyl-7-phenylaminofluoran, etc. The basic dyes useful in this invention are not limited to those exemplified above, and at least two of them can be used in admixture.

The separator or desensitizer can be any of known component agent which exhibit good solubility in both water and organic solvents. Generally, the separators are preferred to be neutral molecules that are without a charge, such as polyalkylene glycol of <1000 Daltons, polyalkylene oxide of <10000 Daltons, block copolymers of polyoxyethylene polyoxypropylene glycol, polyoxyethylene nonylphenyl ether, polyoxyethylene distyrenated phenyl ether, neutral surfactants. Other examples of such separators may include glycerin; dodecylamine; 2,4,4-trimethyl-2-oxazoline; polyolefin glycols such as polyethylene glycol, polypropylene glycol and copolymer of ethylene glycol and propylene glycol; polyoxyethylene lauryl ether, polyoxyethylene oleyl ether, polyoxyethylene nonyl phenyl ether, polyoxyethylene sorbitan monolaurate, polyethylene glycol monostearate.

Generally, the color-developers exhibit good solubility in organic solvents. Examples of suitable developers include bisphenol A, zinc chloride, zinc salicylate, and phenol resins. Other examples of color developing materials to be used conjointly with the lecuo dyes may include: 4-tert-butylphenol, α-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis(6-tert-butyl-3-methylphenol), 4,4'-dihydroxydiphenyl sulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds.

Examples of suitable encapsulating polymers may include, for instance, Gantrez series polymers from International Specialty Products, Inc., Dermacryl 97 from National Starch, and Amphomers from Akzo Nobel. The encapsulation matrix may also be a mixture of various chemicals dissolved in an organic solvent system. Examples of such a system may include organic solvent-based varnishes, such as varnishes made by Sunchemical Co. Examples of polymers and copolymers that are substantially soluble in organic solvents may include: styrene-butadiene copolymers, acrylic acid ester polymers, polyvinyl acetates, polyvinyl chlorides; polyvinylbutyral, polyvinyl acetate, vinyl chloride-vinyl acetate copolymer, acrylic resin, styrene resin, polyester resin, and polyvinyl acetate, vinyl chloridevinyl acetate copolymer, styrene-maleic anhydride copolymer, isobutylene-maleic anhydride copolymer, polyvinyl butyral.

The above composition also contains a volatile organic solvent system. Examples of such volatile organic solvents or a mixing solvent system may include low-molecular weight alcohols, such as butanol, ethanol, propanol, and acetone or tetrahydrofuran or their mixtures.

In addition to ink compositions, the active graphic can also comprise a dye, an adhesive, or any other suitable chemical.

In contrast to active graphics, the term "permanent graphic" is used herein to refer to a graphic that does not substantially change its degree of visibility when the absorbent article is insulted with a body fluid in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature (≅23° C.), for a period of twenty minutes. After 20 minutes the product is removed from the aqueous solution and placed on a TEFLON™ coated fiberglass screen having 0.25 inch openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of 20-20 should make the observations from a distance of 1 meter in an environment providing 30 foot-candles (320 Lux) of illumination. Changes in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. The character graphics can comprise permanent graphics, active graphics, or both permanent and active graphics.

Suitable character graphics can include animals, people, inanimate objects, natural phenomena, cartoon characters, or the like that can or can not be provided with human features such as arms, legs, facial features or the like. For purposes of enhanced toilet training, it may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering.

In general, absorbent articles made in accordance with the present disclosure contain graphics comprising single or multiple images, objects and/or characters. All of the graphics can be assembled together on the absorbent article so as to present an integrated look that depicts a scene. In addition to characters and other images as described above, the scene can include a framing device, outlines, a background, a foreground, and one or more silhouettes.

As used herein, the "background" of a scene is the surface against which represented objects and forms are perceived or depicted. The background is situated behind the location of an image or object. Each scene includes a background. In addition, various elements within the scene may also include a background.

As used herein, the "foreground" describes the location of an image or object which is situated in front of something. As understood by one skilled in the art, an object may be both in the foreground and the background.

As described above, the present disclosure is generally directed to an absorbent article that includes at least one graphic for conveying information. In one embodiment, for instance, the absorbent article includes an outer cover having an interior surface and an exterior surface. An absorbent structure is positioned adjacent to the interior surface of the outer cover. The absorbent article can further include a liquid permeable liner. The absorbent structure can be positioned inbetween the outer cover and the liquid permeable liner. Once assembled, the absorbent structure can include an inside surface that faces the wearer when the article is being worn and an opposite outside surface.

In accordance with the present disclosure, the absorbent article further includes at least one active graphic that appears, disappears or changes color when exposed to an activation agent. The activation agent, for instance, may comprise a body exudate, temperature, a microbial load, ultraviolet light, or a volatile gas. The active graphic includes a visible state where the active graphic is visible from a surface of the absorbent article. The active graphic in accordance with the present disclosure comprises a machine readable code that when in the visible state is configured to provide information to a user when scanned by a suitable reader device. For instance, the code may link a suitable reader device to a website address that provides information related to the absorbent article.

In one embodiment, the machine readable code may comprise a two dimensional code. A two dimensional code, for instance, can store information in multiple ways. For instance, a two dimensional code may store information in rows and columns or in a circular pattern. In another embodiment, the two dimensional code may use color in combination with a direction for storing information. In one embodiment, the two dimensional code may, for instance, comprise a matrix pattern that includes a finder component and an alignment component in addition to data components. The two dimensional code may be readable by an optical reader and may include a uniform resource locator embedded within the data components. The optical reader, which may comprise any suitable mobile device, can be automatically linked to a website address once the two dimensional code is scanned. The website address can then provide information to the user related to the absorbent article.

In an alternative embodiment, instead of linking a user to a website address, information may be encoded in the machine readable code. Once read with a suitable reader device, for instance, the information may immediately become available. In one embodiment, for instance, text can be encoded in the machine readable code.

As described above, the machine readable code comprises an active graphic that disappears, appears, or changes color when contacted with an activation agent. In one embodiment, for instance, the activation agent may comprise a component contained within a body exudate. The active graphic comprised in the machine readable code may change into a visible state or into a more visible state once contacted with the body exudate.

In one embodiment, the active graphic comprising the machine readable code may be incorporated into an overall scene on the absorbent article in order to make the code less noticeable. For instance, in one embodiment, a scene may be printed on the absorbent article that includes various images, such as characters. The machine readable code may be incorporated into the character or incorporated into the background of the scene. In one embodiment, for instance, at least certain components of the scene are comprised of permanent graphics that surround the active graphic that comprises the machine readable code.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
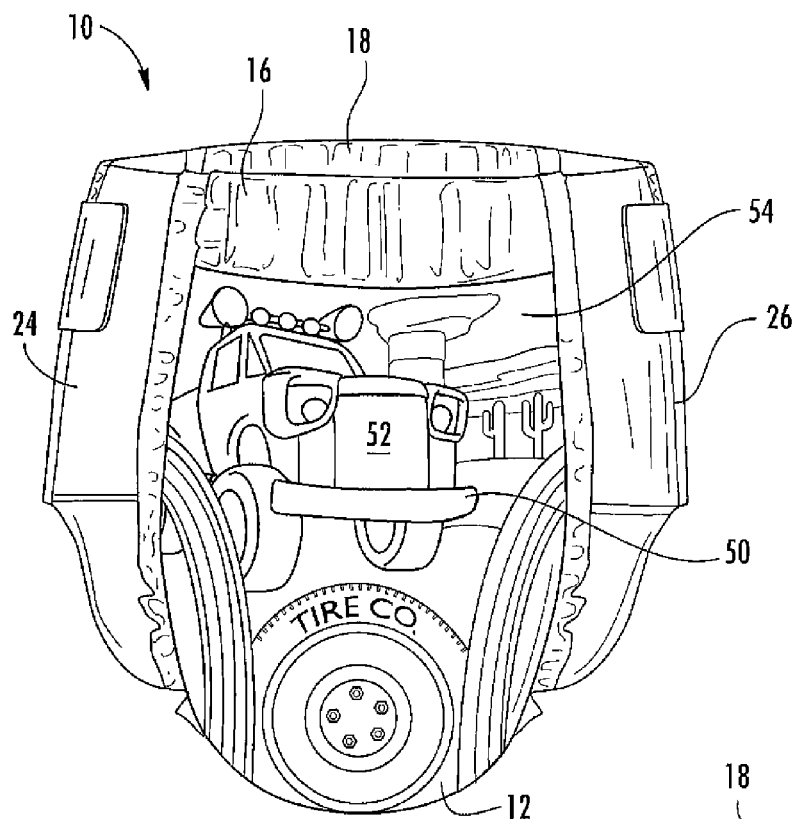
FIG. 1 is a perspective view of one embodiment of an absorbent article made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to an absorbent article that includes an active graphic capable of providing access to information to a user. The information may be related to the product. For example, in one embodiment, the active graphic may comprise a machine readable code. When scanned by a suitable reader device, the machine readable code may directly provide information to a user or direct a user to a website address where the information is contained.

As described above, the machine readable code is contained within an active graphic. In this manner, the machine readable code may initially be visible on the product and then disappear when contacted by an activation agent, may initially be unnoticeable on the product and then change into a visible state when contacted with an activation agent, and/or may change colors when contacted by an activation agent. The activation agent can be any agent that may be present in the environment in which the product is used. In one embodiment, for instance, the activation agent may comprise a body exudate.

In addition to appearing, disappearing or changing color, the active graphic can also be integrated into a scene depicted on the absorbent article. The scene may comprise an aesthetic or decorative pattern or may comprise interrelated images, such as a character graphic appearing in conjunction with foreground graphics and/or background graphics.

As will be described in greater detail below, the machine readable codes of the present disclosure when scanned by a suitable reader device can automatically link a user to a website. Thus, the technology discussed herein makes reference to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein can be implemented using a single server or multiple servers working in combination. Databases and applications can be implemented on a single system or distributed across multiple systems. Distributed components can operate sequentially or in parallel. In one embodiment, for instance, the reader device used for scanning the two dimensional codes may comprise a mobile device, such as a mobile telephone that includes an optical scanner. Alternatively, the reader device may be part of or connected to a personal computer.

Thus, the various reader devices and computer systems discussed herein are not limited to any particular hardware architecture or configuration. Embodiments of the methods and systems set forth herein can be implemented by one or more general-purpose or customized reader devices and/or computing devices adapted for connecting the device to the Internet. Further, when software is used in carrying out the methods of the present disclosure, any suitable programming, scripting, or other type of language or combinations of languages can be used to implement the teachings contained herein.

Figure 2:
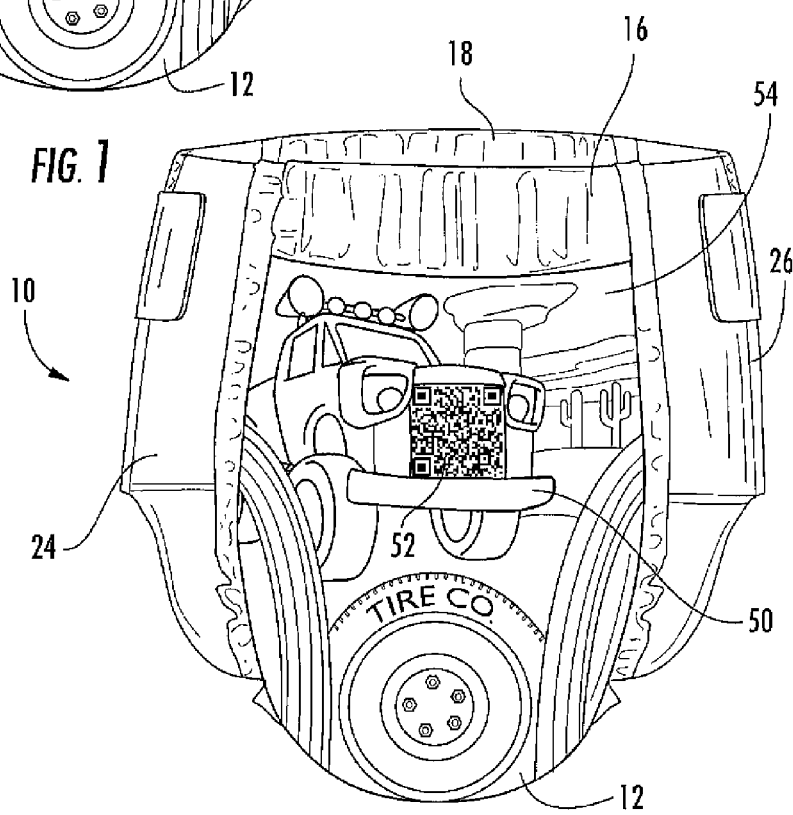
FIG. 2 is a perspective view of the absorbent article illustrated in FIG. 1 showing the appearance of a two dimensional code.
Figure 3:
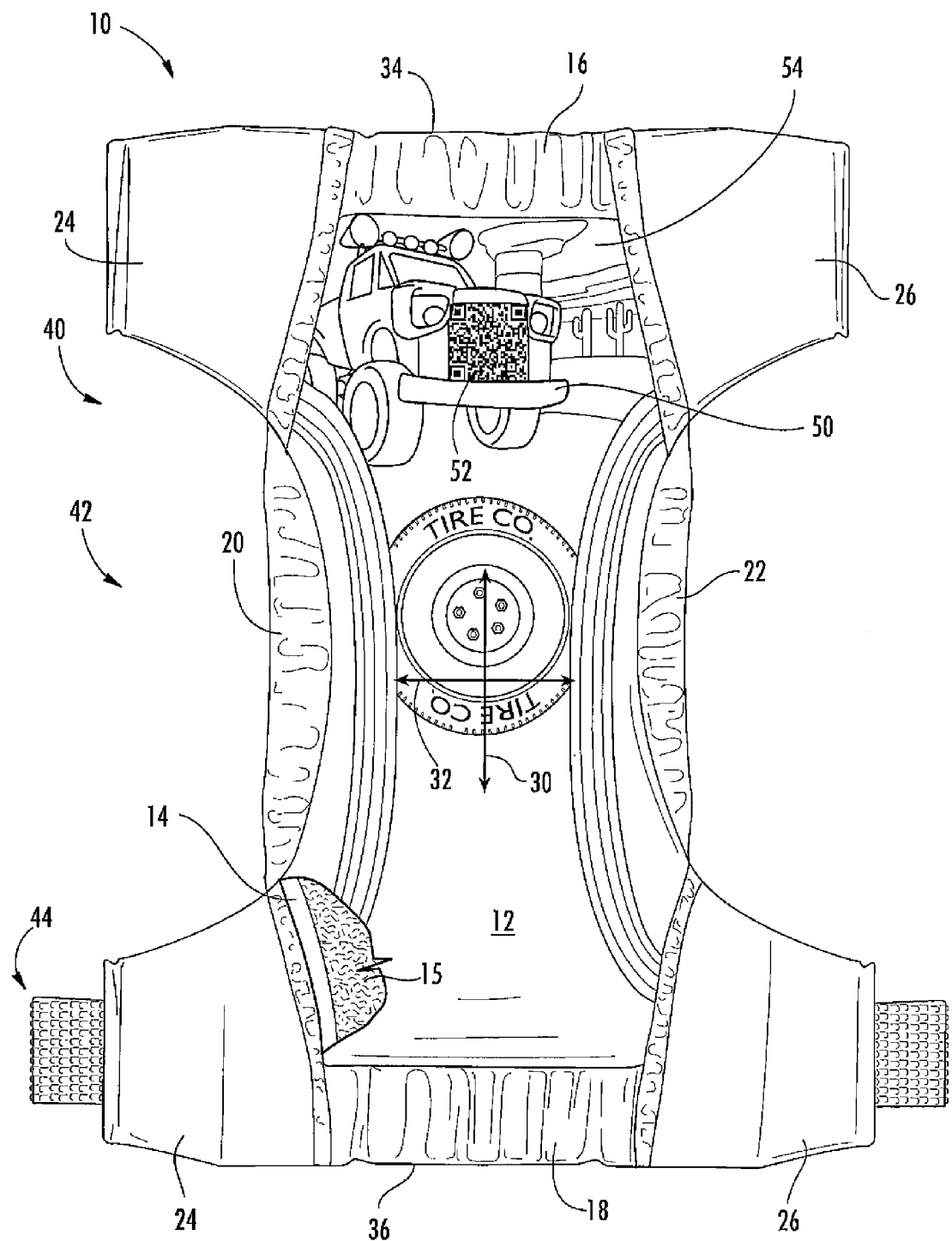
FIG. 3 is a plan view of the absorbent article illustrated in FIG. 1.

Referring to FIGS. 1 through 3, for instance, one embodiment of an absorbent article 10 made in accordance with the present disclosure is shown. In the figures, a child's training pant is generally illustrated. It should be understood, however, that the inventive concepts described herein can be applied to any suitable absorbent article, such as a diaper, an adult incontinence product, a feminine hygiene product or the like.

In the figures, various graphics are shown to be visible from an exterior surface of the absorbent article, such as by being applied to the outer cover. It should be understood, however, that the graphics may also be applied so as to be visible from an inside surface of the article. For instance, when applied to a feminine hygiene product, the graphics may more appropriately be placed to be visible from the inside surface which is adjacent to the body of the wearer. In order to be visible from the interior surface, the active graphics may be applied to a liquid permeable bodyside liner, to a surge layer, to a portion of the absorbent core, or even to the outer cover material in certain embodiments.

Referring to FIG. 3, absorbent articles generally include an outer cover 12 that includes an exterior surface and an interior surface. Located adjacent the interior surface is an absorbent structure 15. Optionally, the absorbent article can also include a liquid permeable inner lining 14. The absorbent structure can be placed in between the outer cover 12 and the inner lining 14. The absorbent article 10 can further include elastic waistbands 16 and 18 and elastic leg members 20 and 22.

The absorbent article 10 as shown in FIG. 1 can be made from various materials. The outer cover 12 may be made from a material that is substantially liquid impermeable, and can be elastic, stretchable or nonstretchable. The outer cover 12 can be a single layer of liquid impermeable material, or may include a multi-layered laminate structure in which at least one of the layers is liquid impermeable. For instance, the outer cover 12 can include a liquid permeable outer layer and a liquid impermeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is suitably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

As described above, the absorbent structure is positioned in between the outer cover and a liquid permeable bodyside liner 14. The bodyside liner 14 is suitably compliant, soft feeling, and non-irritating to the wearer's skin. The bodyside liner 14 can be manufactured from a wide variety of web materials, such as synthetic fibers, natural fibers, a combination of natural and synthetic fibers, porous foams, reticulated foams, apertured plastic films, or the like. Various woven and nonwoven fabrics can be used for the bodyside liner 14. For example, the bodyside liner can be made from a meltblown or spunbonded web of polyolefin fibers. The bodyside liner can also be a bonded-carded web composed of natural and/or synthetic fibers.

A suitable liquid permeable bodyside liner 14 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

The material used to form the absorbent structure, for example, may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web may have a density within the range of about 0.1 to about 0.45 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and suitably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland, Mich., USA.

In addition to cellulosic fibers and superabsorbent materials, the absorbent pad structures may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and alternatively or additionally may provide adherence between facing layers of the folded structure.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be used. For example, an elastomeric coform absorbent structure having from about 35% to about 65% by weight of a wettable staple fiber, and greater than about 35% to about 65% by weight of an elastomeric thermoplastic fiber may be used to define absorbent pad structures according to the invention. Examples of such elastomeric coform materials are provided in U.S. Pat. No. 5,645,542, incorporated herein in its entirety for all purposes. As another example, a suitable absorbent elastic nonwoven material may include a matrix of thermoplastic elastomeric nonwoven filaments present in an amount of about 3 to less than about 20% by weight of the material, with the matrix including a plurality of absorbent fibers and a super-absorbent material each constituting about 20-77% by weight of the material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.1 to about 0.45 grams per cubic centimeter. The absorbent web can alternatively be a foam.

As shown in FIGS. 1 and 2, the absorbent article 10 can include side panels 24 and 26. The side panels 24 and 26 can have a color that blends with the overall scene appearing on the absorbent article. The side panels 24 and 26 can be permanently bonded together or can be releasably attached to one another. In FIG. 3, for instance, the side panels 24 and 26 are shown in an unattached state. In general, the side panels 24 and 26 are made from an elastic material, such as an elastic laminate.

As shown particularly in FIG. 3, the absorbent article 10 defines a longitudinal center line 30, a transverse center line 32, a first or front longitudinal end edge 34, and a second or back longitudinal end edge 36. The longitudinal axis lies in the plane of the article and is generally parallel to a vertical plane that bisects a standing wearer into left and right body halves when the article is worn. The transverse axis lies in the plane of the article generally perpendicular to the longitudinal axis.

In general, the absorbent article along the longitudinal axis can be divided into a front region 40, a back region 44, and a crotch region 42 positioned in between the front region and the back region. In one embodiment, the front region, the crotch region, and the back region can all have approximately the same length in the longitudinal direction.

The absorbent article can also be divided into a front half and a back half. The front half, for instance, may extend in the longitudinal direction from the front edge to the midpoint of the product, while the back half may extend from the back edge to the midpoint of the product.

As shown in FIGS. 1 through 3, the absorbent article 10 includes various graphics. In accordance with the present disclosure, the entire scene displayed on the outer cover of the absorbent article can be made from active graphics or a combination of permanent graphics and active graphics. In the embodiment illustrated, for instance, the scene depicts a focal image which comprises a vehicle character 50. The character 50 appears on a background 54 with further graphics. The background 54, for instance, may provide further scene details. In the embodiment illustrated, for instance, the background 54 depicts a desert setting.

In the embodiment illustrated, the car character 50 and the background 54 may all comprise permanent graphics.

In accordance with the present disclosure, the scene depicted on the absorbent article 10 further includes at least one active graphic 52. As shown, the active graphic 52 is positioned on the grill of the car character 50. In this manner, the active graphic 52 is integrated into the focal image or car character 50.

The active graphic 52 comprises a machine readable code that, when scanned by a suitable reader device, conveys information to the user related to the absorbent article 10. In the embodiment illustrated, the active graphic 52 comprises an appearing graphic that, as shown in FIG. 1, is initially not visible. When contacted with an activation agent, however, the active graphic 52 becomes visible as shown in FIG. 2. In other embodiments, however, the active graphic 52 may initially be visible and then once contacted with an activation agent becomes less noticeable or invisible. In yet another embodiment, the active graphic 52 may change color when contacted with an activation agent. For instance, the active graphic may initially be a dull or less noticeable color and then when contacted with an activation agent may change into a bright or more noticeable color, or vice versus.

The activation agent that is used to cause the active graphic 52 to change in appearance can vary depending upon the particular application and various factors. In general, the activation agent comprises an agent that is present in the environment in which the product is used. In one embodiment, for instance, the activation agent may comprise a body exudate, such as urine or a component in urine. Other activation agents may comprise heat, a change in pH, an oxidant, a reducing agent, a nucleophile, water or humidity, an electrophile, an amine/ketone reaction, electromagnetic radiation such as ultraviolet light, pressure, sound, a gas, or a vapor. In other embodiments, the activation agent may comprise an analyte or a microbial load, which may be contained in a body exudate.

In general, the active graphic 52 can be comprised of an ink that is responsive to the activation agent. Thus, depending upon the desired result, a particular ink composition can be selected that is responsive to the desired activation agent.

The active graphic 52 illustrated in FIG. 2 generally comprises a readable code that can convey information to a user. In one embodiment, for instance, the active graphic can comprise a two dimensional code. Two dimensional codes have evolved from one dimensional codes, such as bar codes. One dimensional bar codes contain small amounts of information in only one direction. Although one dimensional codes may be used in certain embodiments of the present disclosure, one dimensional codes are very limited in the amount of information that can be conveyed to a user.

Two dimensional codes, on the other hand, can store information in at least two directions, such as in a vertical and horizontal direction. Two dimensional codes can also store information in a circular direction. Two dimensional codes can also use color to store information. Various different reader devices exist that are capable of scanning two dimensional codes, such as the one illustrated in FIG. 2. In one embodiment, for instance, the reader device may include a camera that initially captures the two dimensional code in a picture and then runs the image through a decoding algorithm. Such reading devices are typically referred to as optical scanners. The algorithm allows the code to be viewed from any direction. Once decoded, the two dimensional code can either directly provide information to the reader device or link the reader device to a website address. For instance, in one embodiment, the two dimensional code may include a uniform resource locator.

In one embodiment, the two dimensional code can provide hard-links or physical world hyperlinks and allow people to receive information anywhere by simply scanning the code with, for instance, a camera on their cellular phone. Many cellular phones, for instance, are already equipped with reader devices or can be turned into a reader device by downloading a software application. The software is capable of deciphering a picture of the two dimensional code or quick response code and automatically displaying the contents back to the user.

Many machine readable codes can store over 7000 characters in a single image. Many two dimensional codes, for instance, can encode the same amount of information into about one-tenth the amount of space of a one dimensional code.

Another advantage to using a two dimensional code as illustrated in FIG. 2 is the error correction capabilities in the event that part of the code is not readable due to damage or lack of complete contact with an activation agent. In such events, suitable reader devices can still decipher the image. For example, two dimensional codes have four possible levels of error correction: Level L, Level M, Level Q, and Level H which allow for 7%, 15%, 25%, and 30% of the data to be obscured yet still readable. The particular code designed for application for use with the absorbent article can have suitable data allotment for falling within one of the above levels of error correction.

Figure 4:
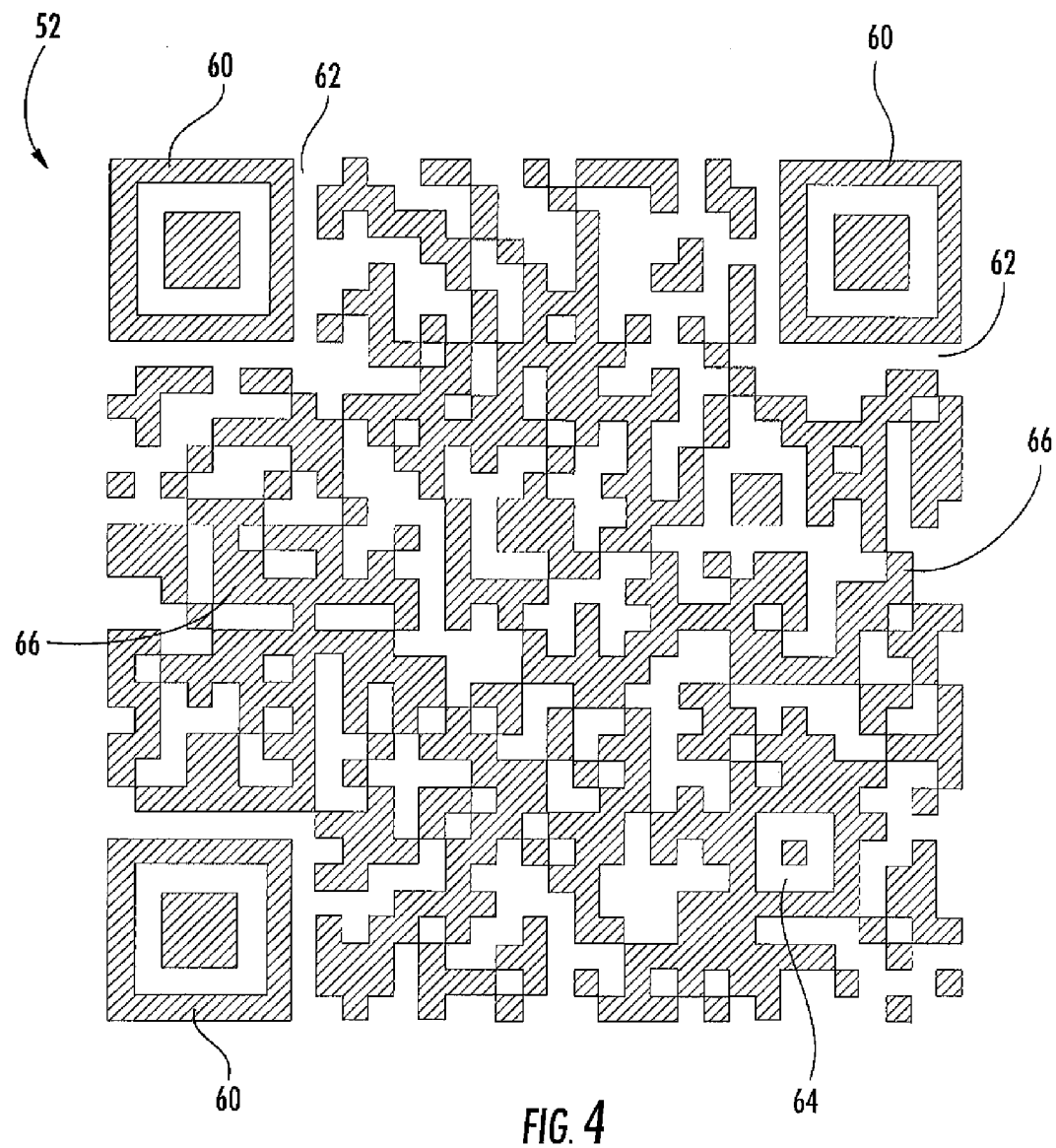
FIG. 4 is a plan view of an active graphic of one embodiment of a two dimensional code that may be used in accordance with the present disclosure.

Referring to FIG. 4, an isolated view of one embodiment of a two dimensional code 52 that may be used in accordance with the present disclosure is shown. In the embodiment illustrated in FIG. 4, the two dimensional code comprises a quick response code. It should be understood, however, that various other two dimensional codes may be used such as circular codes and/or color codes.

As shown in FIG. 4, the two dimensional code includes various components. The different components of the code are used by the reader device to decipher the code. As described above, for instance, the reader device may be programmed with an algorithm that deciphers an image of the code.

As shown in FIG. 4, in this embodiment, the two dimensional code 52 includes a finder component 60 which, in the embodiment illustrated, includes three boxes located in three corners of the image. The finder component 60 is used by an algorithm to determine the position of the code. In certain embodiments, the elements of the finder component 60 may be surrounded by empty margins 62. The empty margins can be used to determine the dimensions of the code.

The two dimensional code 52 can further include an alignment component 64. The alignment component 64 which, in the embodiment illustrated, comprises a smaller box, may be used by an algorithm to correct skew.

In addition to the finder component 60 and the alignment component 64, the two dimensional code may further include a timing pattern which may be used as an offset marker. In one embodiment, for instance, the timing pattern may comprise a pattern that extends between adjacent finder components 60. The two dimensional code 52 further includes data component 66. In the embodiment illustrated, the data component 66 comprise the black and white modules or pixels located throughout the pattern or graphic. The different components are used by a suitable reader for recognizing the image, aligning the image, and then deciphering the data.

U.S. Pat. No. 6,786,412, U.S. Pat. No. 6,997,384, U.S. Pat. No. 5,726,435 and U.S. Patent Application Publication No. 2007/0071320, which are all incorporated herein by reference, describe and discuss various machine readable codes such as the one illustrated in FIG. 4. In one embodiment, a suitable reader device either is programmed with an algorithm or is in communication with a programmable device that includes an algorithm for deciphering the code. Once an image of the code is scanned, the algorithm detects the position of the two dimensional code 52. Next, the code size and coefficient are determined before the cell center position is calculated. Binary data is then generated from the code that is used to reveal information directly or reveal a hyperlink.

As described above, the machine readable code 52 as shown in FIGS. 2 and 4 is comprised of an active graphic that appears, disappears and/or changes color when contacted with an activation agent. Having the machine readable code comprise an active graphic provides numerous advantages and benefits depending upon the particular application. For instance, using an active graphic to display the machine readable code may allow the code to be better integrated into a scene depicted on the absorbent article. As shown in FIGS. 1 through 3, for instance, the absorbent article 10 can include a scene that improves the overall look and aesthetic qualities of the product. In the embodiment illustrated, the machine readable code is not initially visible on the product, thus not interfering with the depicted scene. Once contacted with an activation agent, however, the code appears while still remaining integrated into the scene, by becoming part of the focal image or character.

In other embodiments, the machine readable code may initially appear on the product and then be rendered less visible after the product is used. In this manner, the code can deliver information to the user prior to donning the article. Once the article is placed on a wearer, the machine readable code may contact an activation agent and fade or disappear.

In another embodiment, the machine readable code or active graphic may be configured to appear when a certain condition is met. For example, the activation agent that causes the machine readable code to appear or become more prominent may, in one embodiment, comprise a component in a body exudate, such as an analyte, a microbial load, a pH threshold, or the like that may indicate that the wearer of the absorbent article has a particular condition. Once one of the above activation agents contacts the active graphic, the machine readable code becomes visible to the user. Once scanned by a suitable reader device, the machine readable code can then provide information regarding a possible condition of the user based upon the activation agent.

Having the machine readable code comprise an active graphic can also provide various other benefits. For instance, by making a machine readable code an active graphic, the machine readable code may become a very engaging feature for the wearer of the garment or the caregiver. Ultimately, by making the machine readable code an active graphic, the garment becomes more interactive and thus better for conveying information.

The type of information that is conveyed by the machine readable code can vary depending upon the particular application and the desired result. As described above, in one embodiment, the machine readable code may provide information regarding a condition of the wearer. For instance, the machine readable code may provide information regarding a possible abnormality in a condition of the wearer and provide information not only about the condition but how to treat the condition. In an alternative embodiment, the machine readable code may provide information regarding toilet training. For instance, the information provided by the machine readable code may be for a caregiver for assisting a child in toilet training or may comprise an interactive website that encourages children to become toilet trained.

The machine readable codes can also provide information regarding various incentives. Such an incentive can include a discount or rebate for the absorbent article or for a product relating to the absorbent article. The machine readable code can also link the user to rewards, videos, and other information about the product. In one embodiment, for instance, the machine readable code may provide information not only regarding the product being used but also regarding various other collateral products that may work well in conjunction with the absorbent article. Thus, consumers can become aware of all the different products being offered by the particular manufacturer.

In yet another embodiment, the machine readable code may link a user to various surveys. The surveys, once answered by the user, can help the manufacturer improve the product or improve product service.

In the embodiment illustrated in FIGS. 1 through 3, the active graphic comprising the machine readable code is integrated into the scene depicted upon the absorbent article. In particular, the machine readable code 52 is incorporated into the focal image, which, in the embodiment illustrated, comprises a character vehicle 50.

It should be understood, however, that the machine readable code may be placed at any suitable location on the absorbent article. For instance, for adult incontinence products, the machine readable code may comprise the only graphic appearing on the absorbent article. In other embodiments, the absorbent article may include a scene wherein the machine readable code is incorporated into a foreground image or into a background image.

Figure 5:
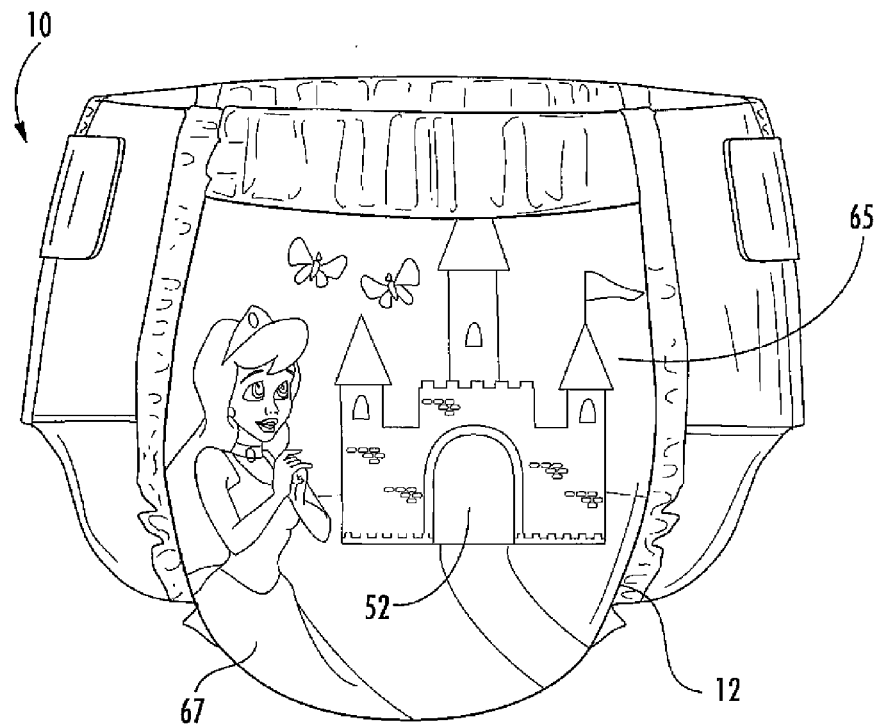
FIG. 5 is a perspective view of another embodiment of an absorbent article made in accordance with the present disclosure.
Figure 6:
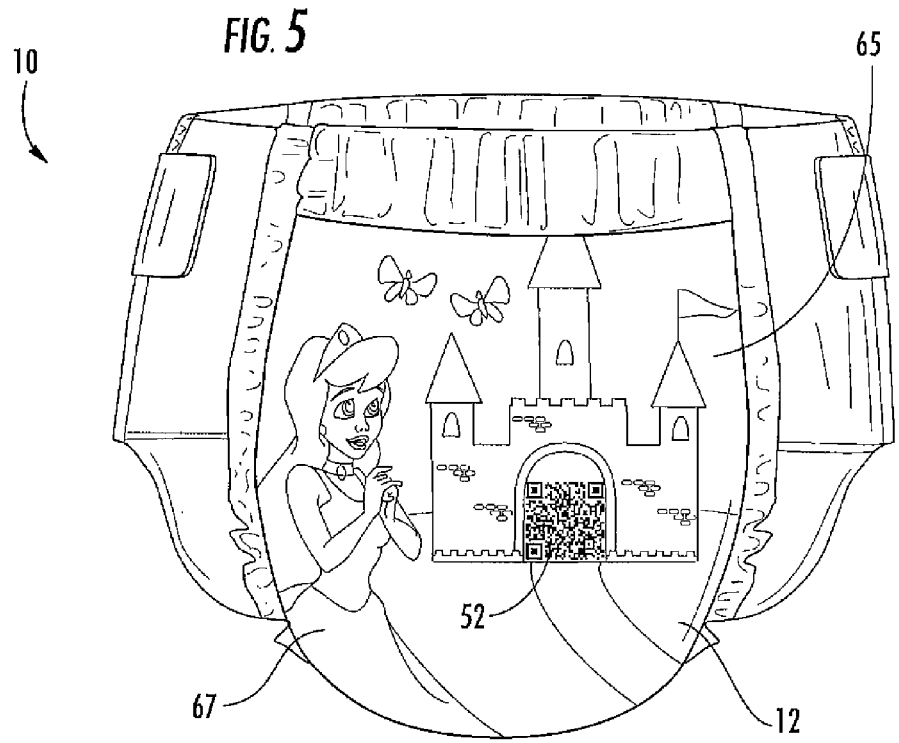
FIG. 6 is a perspective view of the absorbent article illustrated in FIG. 5 showing the appearance of a two dimensional code.

Referring to FIGS. 5 and 6, another embodiment of an absorbent article 10 made in accordance with the present disclosure is shown. In this embodiment, the outer cover 12 of the absorbent article 10 depicts another character scene. The character scene includes a character surrounded by an integrated background 65 including various related objects and images. In particular, the scene is intended to represent a princess 67 surrounded by a background 65 comprised of butterflies and a castle. The princess 67 can be comprised of permanent graphics, active graphics, or a combination of permanent graphics and active graphics. Similarly, the background images 65 can also be comprised of permanent graphics, active graphics, or a combination of permanent and active graphics.

The absorbent article 10 in FIG. 5 is shown in a dry, initial state. FIG. 6, on the other hand, illustrates the absorbent article 10 once contacted with an activation agent. As shown in FIG. 6, once contacted with an activation agent, a machine readable code comprising an active graphic 52 appears. In the embodiment illustrated in FIGS. 5 and 6, the active graphic 52 comprising the machine readable code is incorporated into or integrated into a background image.

The absorbent article illustrated in FIGS. 1 through 3 that includes a vehicle character may be designed for use by boys, while the princess scene depicted in FIGS. 5 and 6 may be particularly well suited for girls. It should be understood, however, that the inventive concepts described in the embodiments can be used for either sex by designing the appropriate scene and using the appropriate colors.

The active graphics and permanent graphics used to form the scenes as shown in the figures can be applied to the absorbent article in different ways. In one embodiment, for instance, the outer cover 12 of the absorbent article includes multiple layers. The outer cover 12 may include, for instance, an inner water impermeable film and an outer water permeable layer that may comprise, for instance, a nonwoven layer. The inner film may be clear such that graphics printed on the inner film can be visible from the exterior surface of the outer cover. As can be appreciated, the active graphics should be applied to the absorbent article such that they contact the activation agent when present. In this regard, the active graphics may be printed on the interior surface of the outer cover such as on the inner surface of the inner film. The permanent graphics, however, can be printed on other layers of the outer cover. The permanent graphics, for instance, can be printed on the exterior surface of the outer cover, or can be printed on any of the interior layers either on the side facing the wearer or on the side opposite the wearer.

When the active graphics are to be visible from an interior side of the garment, the active graphics can be applied to a bodyside liner, a surge material, a rap sheet that surrounds an absorbent structure, or may even be applied to the outer cover as long as the active graphics are visible from the interior.

Another consideration when determining the location of the machine readable code on the absorbent article is the ability of the machine readable code to be scanned by a suitable reader device. Thus, in one embodiment, the machine readable code is placed as far as possible from the mid line of the absorbent article while still being placed in a position that contacts the activation agent when present.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
   an outer cover having an interior surface and an exterior surface;
   an absorbent structure positioned adjacent to the interior surface of the outer cover, the absorbent article including an inside surface that faces a wearer and an opposite outside surface;
   at least one active graphic that includes a visible state where the active graphic is visible from a surface of the absorbent article, the active graphic comprising a machine readable code comprising a two dimensional code that, when in the visible state, is configured to provide information related to the absorbent article when scanned by a suitable reader device; and
   at least one permanent graphic, wherein the permanent graphic is interrelated to the at least one active graphic.

2. An absorbent article as defined in claim 1, wherein the active graphic comprises an appearing graphic that appears and assumes the visible state when exposed to an activation agent.

3. An absorbent article as defined in claim 1, wherein the active graphic comprises a disappearing graphic that converts from the visible state to an invisible state when activated by an activation agent.

4. An absorbent article as defined in claim 1, wherein the active graphic comprises a color changing graphic that changes from an initial state to a second state when exposed to an activation agent.

5. An absorbent article as defined in claim 1, wherein the machine readable code uses color to encode information.

6. An absorbent article as defined in claim 1, wherein the machine readable code stores information in a circular pattern.

7. An absorbent article as defined in claim 1, wherein the machine readable code is encoded with a uniform resource locator.

8. An absorbent article as defined in claim 1, wherein the machine readable code of the active graphic stores information in at least a vertical direction and in a horizontal direction.

9. An absorbent article as defined in claim 1, wherein the active graphic appears, disappears or changes color when exposed to an activation agent comprising a body fluid.

10. An absorbent article as defined in claim 1, wherein the two dimensional code of the active graphic comprises a matrix pattern including a finder component and an alignment component in addition to data components.

11. An absorbent article as defined in claim 1, wherein the active graphic appears, disappears or changes color when exposed to an activation agent that comprises temperature, ultraviolet light, a volatile gas, an analyte or a microbial load.

12. An absorbent article as defined in claim 1, wherein the active graphic is visible from an outside surface on the absorbent article.

13. An absorbent article as defined in claim 1, wherein the active graphic is visible from an inside surface on the absorbent article.

14. An absorbent article as defined in claim 1, wherein the absorbent article further comprises graphics that depict a scene, the active graphic comprising the machine readable code being integrated into the scene.

15. An absorbent article as defined in claim 14, wherein the scene depicts one or more characters.

16. An absorbent article as defined in claim 14, wherein the scene includes at least one focal image and a background, the machine readable code being integrated into the background.

17. An absorbent article as defined in claim 15, wherein the machine readable code is integrated into the character.

18. An absorbent article as defined in claim 14, wherein the active graphic and the scene are visible from an outside surface of the absorbent article.

19. An absorbent article as defined in claim 1, wherein the activation agent comprises a body fluid that indicates the possibility of a condition and wherein the information provided by the machine readable code is related to the condition.

20. An absorbent article as defined in claim 1, wherein when scanned by a suitable reader device, the machine readable code links the reader device to a website address.

21. An absorbent article as defined in claim 20, wherein the website address provides a user with incentives.

22. An absorbent article as defined in claim 21, wherein the incentives comprise coupons or rebates for products.

23. An absorbent article as defined in claim 20, wherein the website address provides a user with information regarding a physiological condition.

24. An absorbent article as defined in claim 20, wherein the website address provides a user with information regarding an analytical assessment/result done as a result of urination.

* * * * *